US00PP32444P2

(12) United States Plant Patent

Klemm et al.

(10) Patent No.: US PP32,444 P2
(45) Date of Patent: Nov. 10, 2020

(54) *DIANTHUS* PLANT NAMED 'KLEDG19303'

(50) Latin Name: *Dianthus cultivars*
Varietal Denomination: KLEDG19303

(71) Applicant: Klemm+Sohn GmbH & Co. KG, Stuttgart (DE)

(72) Inventors: Nils Klemm, Stuttgart (DE); Lena Thiede, Bempflingen (DE)

(73) Assignee: Klemm+Sohn GmbH & Co., KG, Stuttgart (DE)

( * ) Notice: Subject to any disclaimer, the term of this patent is extended or adjusted under 35 U.S.C. 154(b) by 0 days.

(21) Appl. No.: 16/873,298

(22) Filed: Mar. 12, 2020

(51) Int. Cl.
*A01H 6/30* (2018.01)
*A01H 5/02* (2018.01)

(52) U.S. Cl.
USPC ..... Plt./277

(58) Field of Classification Search
USPC ..... Plt./277
See application file for complete search history.

*Primary Examiner* — Annette H Para
(74) *Attorney, Agent, or Firm* — Weatherly IP Solutions, LLC; James Weatherly

(57) ABSTRACT

A new *Dianthus* plant named 'KLEDG19303' particularly distinguished by single flowers with a magenta flower color with a purple center, a maculated flower pattern and green-grey leaf color, is disclosed.

1 Drawing Sheet

Genus and species: *Dianthus cultivars*.
Variety denomination: 'KLEDG19303'.

BACKGROUND OF VARIETY 'KLEDG19303'

The present invention comprises a new and distinct variety of *Dianthus*, botanically known as *Dianthus cultivars* and hereinafter referred to by the variety name 'KLEDG19303'. 'KLEDG19303' is a selection that resulted from an open pollination of the proprietary female *Dianthus* line 'DSU-2011-0033' (unpatented) and the proprietary male *Dianthus* line 'DSS-2011-0047'.

In May of 2014, the proprietary female *Dianthus* line 'DSU-2011-0033' and the proprietary male *Dianthus* line 'DSS-2011-0047' were cross pollinated in Stuttgart, Germany and seeds were obtained. The seeds were sown and plants were grown for evaluation. A plant line was selected in June of 2015 in Stuttgart, Germany, and named 'KLEDG19303'. In September of 2015, 'KLEDG19303' was first vegetatively propagated by vegetative cuttings. 'KLEDG19303' was found to reproduce true to type in successive generations of asexual propagation via vegetative cuttings in Stuttgart, Germany and Latina, Italy.

SUMMARY OF VARIETY 'KLEDG19303'

The following are the most outstanding and distinguishing characteristics of this new variety when grown under normal horticultural practices in Latina, Italy.

1. Single flowers with a magenta flower color with a purple center;
2. A maculated flower pattern; and
3. Green-grey leaf color.

DESCRIPTION OF THE PHOTOGRAPH

This new *Dianthus* plant is illustrated by the accompanying photograph which shows the overall plant habit of the variety 'KLEDG19303' grown in a pot. The photograph is of a 14-week-old plant in Stuttgart, Germany under greenhouse conditions in April 2018.

DESCRIPTION OF THE NEW VARIETY 'KLEDG19303'

The following detailed descriptions set forth the distinctive characteristics of 'KLEDG19303'. Data was collected on eight-month-old potted plants in June 2019 in Latina, Italy. Color references are to The R.H.S. Colour Chart of The Royal Horticultural Society of London (R.H.S.), 5$^{th}$ edition.

Classification:
- *Family*.—Caryophyllaceae.
- *Species*.—*Dianthus cultivars*.
- *Common name*.—Pot carnation.
- *Parentage*.—Female: Proprietary *Dianthus* line 'DSU-2011-0033' (unpatented). Male: Proprietary *Dianthus* line 'DSS-2011-0047' (unpatented).

Propagation:
- *Type*.—Vegetative cuttings.
- *Time to produce a rooted young plant*.—14 to 18 days.
- *Root description*.—Young roots: RHS 161D. Mature roots: RHS 199C.
- *Rooting habit*.—Lanceolate.

Plant description:
- *Plant form*.—Upright.
- *Plant height*.—16.0 cm to 19.0 cm.
- *Plant diameter or spread*.—16.0 cm to 18.0 cm.

Lateral branches:
- *Length*.—5.0 cm to 10.0 cm.
- *Diameter*.—2.0 cm.
- *Internode length*.—2.0 cm to 4.0 cm.
- *Number of internodes per branch/stem*.—3 to 5.
- *Node length*.—0.2 cm to 0.4 cm.
- *Node diameter*.—0.2 cm to 0.4 cm.
- *Texture*.—Smooth.
- *Color*.—RHS 146C.
- *Branch/stem*.—Solid.

Foliage description:

*Arrangement*.—Opposite.

*Length*.—1.0 cm to 4.0 cm.

*Width*.—0.2 cm to 0.4 cm.

*Shape*.—Lanceolate.

*Apex*.—Acute.

*Base*.—Obtuse.

*Margin*.—Entire.

*Texture*.—Upper and lower surfaces: Smooth.

*Immature leaf color*.—Upper surface: RHS 146A. Lower surface: RHS 146B.

*Mature leaf color*.—Upper and lower surfaces: RHS 189A.

*Venation pattern*.—No venation.

Flower description:

*Quantity of petals and arrangement*.—5.

*Corolla height*.—0.8 cm to 1.2 cm.

*Petal length*.—2.8 cm to 3.2 cm.

*Petal width*.—1.0 cm to 1.5 cm.

*Petal shape*.—Spoon shaped.

*Petal apex*.—Obtuse.

*Petal base*.—Acute.

*Petal margin*.—Serrated.

*Depth of petal margin*.—Shallow.

*Petal texture*.—Upper and lower surfaces: Smooth.

*Petal color*.—Immature and Mature: Upper surface: RHS 74A and RHS 71B macule. Lower surface: RHS 73A.

*Calyx*.—Quantity of sepals and arrangement: Composed of 5 sepals. Shape: Campanulate. Calyx height: 1.8 cm to 2.2 cm. Calyx diameter (at the apex): 0.4 cm to 0.6 cm. Sepal texture: Upper and lower surfaces: Smooth. Sepal color: Upper surface: RHS 137A. Lower surface: RHS 137D.

Peduncles:

*Length*.—1.0 cm to 2.0 cm (last internode), whole stem 10.0 cm.

*Diameter*.—0.1 cm to 0.2 cm.

*Strength*.—Moderate.

*Texture*.—Smooth.

*Color*.—RHS 189A.

Reproductive organs:

*Stamens*.—Quantity per flower: 7 to 10. Filament length: 1.5 cm to 2.0 cm. Filament color: RHS 155D. Anther length: 0.2 cm. Anther diameter: 0.1 cm. Anther color: RHS 85C. Pollen amount: Moderate.

*Pistils*.—Quantity per flower: Two styles. Pistil length: Not observed. Style length: 1.0 cm to 1.5 cm. Style color: RHS 155D. Stigma shape: Filamentous. Stigma color: RHS 85C. Ovary size: 0.5 cm to 0.7 cm. Ovary shape: Oval. Ovary color: RHS 145C.

Fruit and seed set: Seed sometimes observed.

Disease and insect/pest resistance: No special observations were made.

COMPARISON OF 'KLEDG19303' WITH PARENTAL LINES AND KNOWN VARIETY

When 'KLEDG19303' is compared to the female parental line 'DSU-2011-0033' and the male parental line 'DSS-2011-0047', the following differences are noted in Table 1:

TABLE 1

Comparison with Parental Lines

| Trait or characteristic | 'KLEDG19303' | Female parent | Male Parent |
|---|---|---|---|
| Flower color | Magenta, purple center | Pink purple star | Light pink, pink star |
| Flower pattern | Macule | Star | Star |

When 'KLEDG19303' is compared to the commercial line 'KLEDG18305' (U.S. Plant Pat. No. 31,019), the following differences are noted in Table 2:

TABLE 2

Comparison with Similar Variety

| Trait or characteristic | 'KLEDG19303' | Commercial line: 'KLEDG18305' |
|---|---|---|
| Flower type | Single | Single |
| Flower color | Magenta, purple center | Pink with purple ring |
| Leaf color | Green-Grey | Dark green |

We claim:

1. A new and distinct variety of *Dianthus* plant named 'KLEDG19303' as shown and described herein.

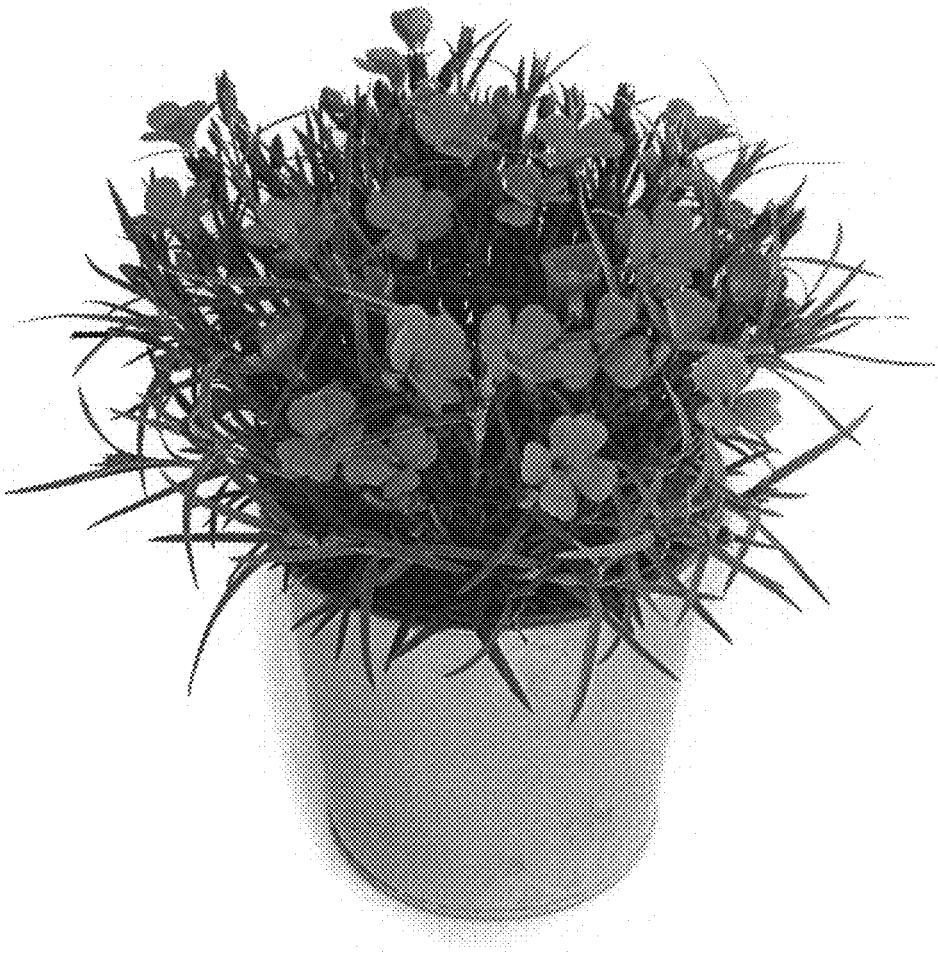

* * * * *